United States Patent
He et al.

(10) Patent No.: US 10,950,342 B2
(45) Date of Patent: Mar. 16, 2021

(54) PORTABLE MEDICAL SUPPORT SYSTEM WITH ANCILLARY VIEWING MODE AND METHOD OF OPERATION THEREOF

(71) Applicant: KONINKLIJKE PHILIPS N.V., Eindhoven (NL)

(72) Inventors: Dongxing He, Carlsbad, CA (US); Norbert Daberko, Carlsbad, CA (US); Oliver Smith, Valley Center, CA (US)

(73) Assignee: Koninklijke Philips N.V., Eindhoven (NL)

( * ) Notice: Subject to any disclaimer, the term of this patent is extended or adjusted under 35 U.S.C. 154(b) by 309 days.

(21) Appl. No.: 15/546,811

(22) PCT Filed: Feb. 4, 2016

(86) PCT No.: PCT/EP2016/052321
§ 371 (c)(1),
(2) Date: Jul. 27, 2017

(87) PCT Pub. No.: WO2016/128280
PCT Pub. Date: Aug. 18, 2016

(65) Prior Publication Data
US 2018/0021534 A1    Jan. 25, 2018

Related U.S. Application Data

(60) Provisional application No. 62/115,946, filed on Feb. 13, 2015.

(51) Int. Cl.
*G16H 40/63* (2018.01)
*G06F 3/14* (2006.01)
*A61M 16/00* (2006.01)

(52) U.S. Cl.
CPC .......... *G16H 40/63* (2018.01); *A61M 16/024* (2017.08); *G06F 3/1423* (2013.01);
(Continued)

(58) Field of Classification Search
CPC ........ A61M 16/024; A61M 2205/3569; A61M 2205/505; A61M 2205/8212;
(Continued)

(56) References Cited

U.S. PATENT DOCUMENTS 5,685,314 A * 11/1997 Geheb .................... G16H 40/63
600/513
5,687,717 A * 11/1997 Halpern ............... A61B 5/0205
600/300

(Continued)

*Primary Examiner* — Valerie L Woodward
*Assistant Examiner* — Nathan M Le
(74) *Attorney, Agent, or Firm* — Daniel H. Brean

(57) ABSTRACT

A medical ventilator (100, 200) including a first user interface (114) having a touch-sensitive display having a display area; and at least one controller (104) which determines whether a second user interface (122, 222) having a touch-sensitive display is coupled to the medical ventilator, enables the first user interface when it is determined that the second user interface is not coupled to the medical ventilator, and enables the second user interface when it is determined that the second user interface is coupled to the medical ventilator.

10 Claims, 5 Drawing Sheets

(52) U.S. Cl.
CPC ............... *A61M 2205/3569* (2013.01); *A61M 2205/505* (2013.01); *A61M 2205/8212* (2013.01); *G09G 2330/02* (2013.01); *G09G 2330/021* (2013.01)

(58) Field of Classification Search
CPC .............. G06F 3/1423; G09G 2330/02; G09G 2330/021; G16H 40/63
See application file for complete search history.

(56) References Cited

U.S. PATENT DOCUMENTS

| | | | |
|---|---|---|---|
| 6,201,983 B1 | 3/2001 | Hauman et al. | |
| 6,339,410 B1* | 1/2002 | Milner | G09B 21/00 |
| | | | 345/1.1 |
| 7,117,438 B2 | 10/2006 | Arnett et al. | |
| 8,302,600 B2* | 11/2012 | Andrieux | H01M 10/42 |
| | | | 128/202.22 |
| 8,312,877 B2 | 11/2012 | Cavallaro et al. | |
| 8,597,198 B2* | 12/2013 | Sanborn | A61B 5/08 |
| | | | 600/538 |
| 8,777,923 B2 | 7/2014 | Katz et al. | |
| 9,384,549 B2* | 7/2016 | Leonhardt | G06T 7/0016 |
| 2002/0044059 A1* | 4/2002 | Reeder | G16H 40/67 |
| | | | 340/573.1 |
| 2005/0000519 A1 | 1/2005 | Friberg et al. | |
| 2005/0051168 A1* | 3/2005 | DeVries | A61M 16/0063 |
| | | | 128/204.21 |
| 2005/0133027 A1 | 6/2005 | Elaz et al. | |
| 2006/0144396 A1* | 7/2006 | DeVries | A61M 16/0057 |
| | | | 128/204.21 |
| 2007/0272242 A1* | 11/2007 | Sanborn | A61M 16/142 |
| | | | 128/204.23 |
| 2007/0274693 A1* | 11/2007 | Farbarik | F04D 25/0673 |
| | | | 388/806 |
| 2008/0086691 A1* | 4/2008 | Hopermann | G06F 19/3418 |
| | | | 715/736 |
| 2009/0058635 A1* | 3/2009 | LaLonde | G08C 17/02 |
| | | | 340/539.11 |
| 2010/0078026 A1* | 4/2010 | Andrieux | A61M 16/0465 |
| | | | 128/204.21 |
| 2010/0130872 A1 | 5/2010 | Irisawa | |
| 2011/0126829 A1 | 6/2011 | Carter et al. | |
| 2011/0227739 A1* | 9/2011 | Gilham | G16H 40/63 |
| | | | 340/573.1 |
| 2011/0259332 A1* | 10/2011 | Sanchez | G16H 40/63 |
| | | | 128/204.21 |
| 2011/0265024 A1* | 10/2011 | Leone | A61M 16/0051 |
| | | | 715/771 |
| 2012/0050183 A1* | 3/2012 | Lee | G06F 3/1423 |
| | | | 345/173 |
| 2012/0096381 A1 | 4/2012 | Doyle et al. | |
| 2013/0025591 A1* | 1/2013 | Clark | A61M 16/125 |
| | | | 128/202.26 |
| 2013/0032147 A1* | 2/2013 | Robinson | A61M 16/021 |
| | | | 128/204.18 |
| 2013/0032149 A1* | 2/2013 | Robinson | A61B 5/08 |
| | | | 128/204.21 |
| 2013/0176230 A1* | 7/2013 | Georgiev | A61B 5/04288 |
| | | | 345/173 |
| 2013/0235080 A1* | 9/2013 | Robinson | A61M 1/3666 |
| | | | 345/634 |
| 2013/0262730 A1* | 10/2013 | Al-Ali | A61B 7/003 |
| | | | 710/303 |
| 2013/0273008 A1 | 10/2013 | Lemper | |
| 2013/0324788 A1* | 12/2013 | Holley | A61M 16/0633 |
| | | | 600/28 |
| 2013/0333703 A1* | 12/2013 | Wallace | A61M 16/0051 |
| | | | 128/204.23 |
| 2014/0235975 A1* | 8/2014 | Carnes | A61B 5/0022 |
| | | | 600/323 |
| 2015/0120067 A1* | 4/2015 | Wing | H02J 7/0013 |
| | | | 700/282 |

* cited by examiner

PORTABLE MEDICAL SUPPORT SYSTEM WITH ANCILLARY VIEWING MODE AND METHOD OF OPERATION THEREOF

CROSS-REFERENCE TO PRIOR APPLICATIONS

This application is the U.S. National Phase application under 35 U.S.C. § 371 of International Application No. PCT/EP2016/052321, filed on Feb. 4, 2016, which claims the benefit of U.S. Provisional Patent Application No. 62/115,946, filed on Feb. 13, 2015. These applications are hereby incorporated by reference herein.

The present system relates to a medical support system with a remote imaging mode for selecting imaging devices and, more particularly, to a medical support system with an integrated system for coupling and controlling a touch-screen remote display, and a method of operation thereof.

Medical support systems such as portable mechanical ventilators typically have a small display to reduce size and weight of the ventilators so that they may be easily handled for use. Although, these small displays reduce the size and weight of these ventilators, they provide a screen with a limited size which can be difficult to view and only provides limited functionality. Further, because of limited display capabilities of these screens, it may be difficult as well as time consuming to setup and configure the ventilators. Further, it may be difficult to view a current status of the ventilators during use. Accordingly, embodiments of the present system may overcome these and/or other disadvantages in the prior art.

The system(s), device(s), method(s), arrangements(s), user interface(s), computer program(s), processes, etc. (hereinafter each of which will be referred to as system, unless the context indicates otherwise), described herein address problems in prior art systems.

In accordance with embodiments of the present system, there is disclosed a medical ventilator, including a first user interface having a touch-sensitive display having a display area; and at least one controller which determines whether a second user interface having a touch-sensitive display is coupled to the medical ventilator, enables the first user interface when it is determined that the second user interface is not coupled to the medical ventilator, and enables the second user interface when it is determined that the second user interface is coupled to the medical ventilator. The medical ventilator may include a unitary display coupler configured to couple the second user interface to the medical ventilator. A display interface may be configured to receive an end of the unitary display coupler. The unitary display coupler may couple power, video, and control signals to the second user interface.

In embodiments, the at least one controller may generate a power good indicator (PGI) based upon characteristics of power supplied by the ventilator to the second user interface. The system be configured so that when the second user interface is enabled, the at least one controller may determine whether the power good indicator (PGI) is generated, and shut down the second user interface when it is determined that the power good indicator (PGI) is not generated. When the second user interface is enabled, the at least one controller may further determine whether the second user interface is decoupled from the ventilator. When the at least one controller determines that the second user interface is decoupled from the ventilator, the controller may enable and/or re-enable the first user interface. The second user interface may include a display having a display area which is larger than the display area of the first user interface. The at least one controller may generate a first graphical user interface (GUI) when the first user interface is enabled and may generate a second GUI different from the first graphical user interface when the second user interface is enabled. The first GUI may include menu items which are defined for the first user interface and the second GUI may include menu items which are defined for the second user interface.

The present invention is explained in further detail in the following exemplary embodiments and with reference to the figures, where identical or similar elements may be partly indicated by the same or similar reference numerals, and the features of various exemplary embodiments being combinable. In the drawings.

The following are descriptions of illustrative embodiments that when taken in conjunction with the following drawings will demonstrate the above noted features and advantages, as well as further ones. In the following description, for purposes of explanation rather than limitation, illustrative details are set forth such as architecture, interfaces, techniques, element attributes, etc. However, it will be apparent to those of ordinary skill in the art that other embodiments that depart from these details would still be understood to be within the scope of the appended claims. Moreover, for the purpose of clarity, detailed descriptions of well known devices, circuits, tools, techniques, and methods are omitted so as not to obscure the description of the present system. It should be expressly understood that the drawings are included for illustrative purposes and do not represent the entire scope of the present system. In the accompanying drawings, like reference numbers in different drawings may designate similar elements. The term and/or and formatives thereof should be understood to mean that only one or more of the recited elements may need to be suitably present (e.g., only one recited element is present, two of the recited elements may be present, etc., up to all of the recited elements may be present) in a system in accordance with the claims recitation and in accordance with one or more embodiments of the present system.

Figure 1:
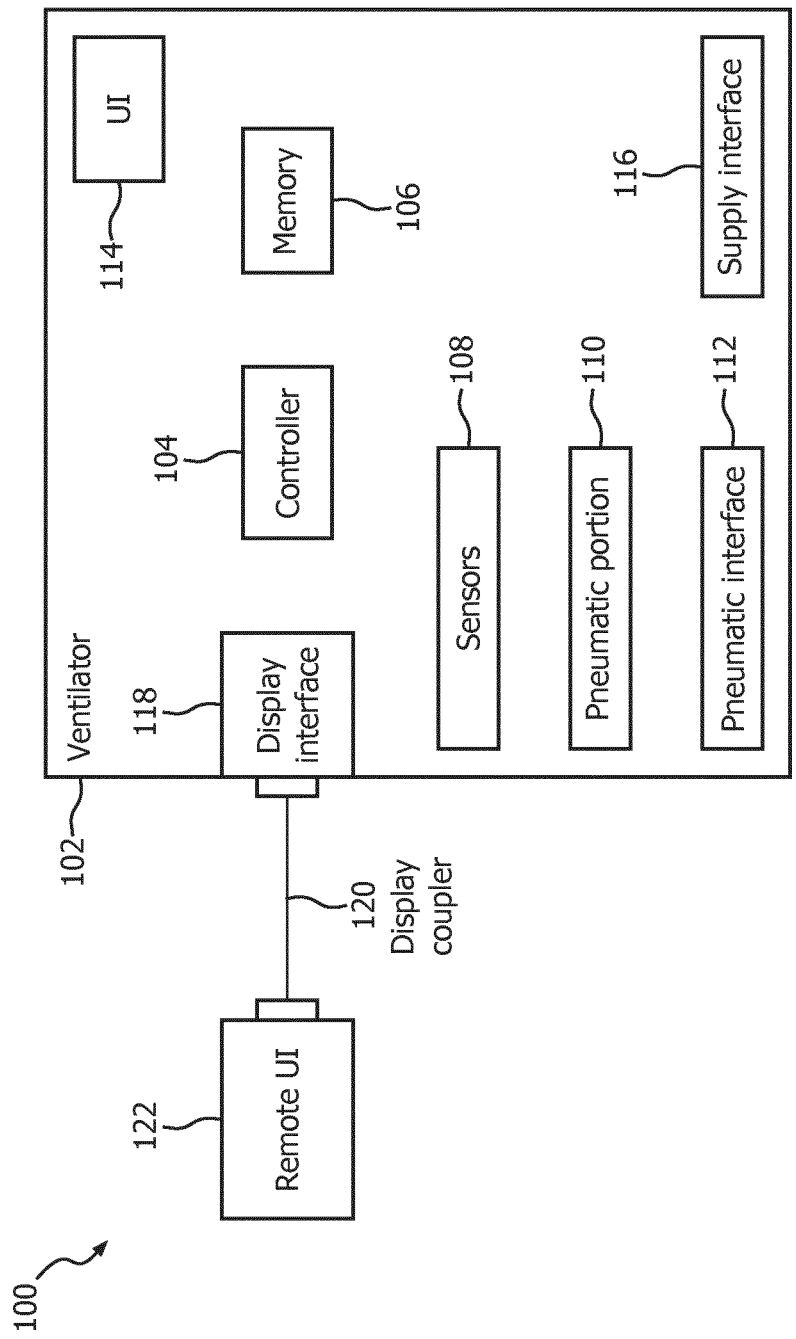
FIG. 1 shows a schematic block diagram of a portion of a ventilator system operating in accordance with embodiments of the present system.

FIG. 1 shows a schematic block diagram of a portion of a ventilator system 100 (hereinafter system 100) operating in accordance with embodiments of the present system. The system 100 may include one or more of a ventilator 102, a user interface (UI) 114, controller 104, a memory 106, sensors 108, a pneumatic portion 110, a gas supply interface 116, a pneumatic interface 112, a display interface 118, a display coupler 120, and a remote display 122. The user interface 114 may include a local touch-screen display and/or hard or soft keys. The local display may be referred to as a primary display or BDU. The remote display may be referred to as a secondary display or a LUI.

The memory 106 may include any suitable memory which may store information such as information generated by the system 100, applications, user information (e.g., user settings, etc.) and/or any other information used by the system 100. The memory 106 may include local, singular, and/or distributed memories operating in accordance with embodiments of the present system. The memory 106 may include transient and/or non-transient memories. Further, the memory 106 may include program and/or program portions. The program and/or program portions contained in the memory 106 may configure the controller 104 to implement the methods, operational acts, and functions disclosed herein. The memory 106 may be implemented as electrical, magnetic or optical memory, or any combination of these or other types of storage devices. As used herein, the term "memory" should be construed broadly enough to encompass any information able to be read from or written to an address in an addressable space accessible by the controller 104. With this definition, it should be understood that information accessible through a network such as a local area network (LAN), a wide area network (WAN), the internet, an multi-master-multi-slave network (e.g., $I^2C$, etc.), a proprietary network, etc., may be considered to still be within the memory, for instance, because the controller 104 may retrieve the information from the network for operation in accordance with embodiments of the present system.

The controller 104 may control the overall operation of the system 100 in accordance with embodiments of the present system. For example, the controller 104 may control one of more of the ventilator 102, the user interface (UI) 114, the memory 106, the sensors 108, the pneumatic portion 110, the gas supply interface 116, the pneumatic interface 112, the display interface 118, the display coupler 120, and the remote display 122. The controller 104 may be programmed to perform one or more processes and/or acts of the present system. Accordingly, the controller 104 may perform one or more algorithms of the present system. For example, the controller may determine whether the remote display 122 is coupled to the display interface 118 and may perform certain actions based upon the determination as discussed herein.

The controller 104 may be operable to provide control signals and/or perform operations in response to input signals from a user input device and/or in response to executing instructions stored in the memory 106 such as application data as well as other data related to the described operation. The application data and other data may be received by the controller 104 to configure (e.g., program) the controller 104 to perform operation acts in accordance with the present system. The controller 104 so configured becomes a special purpose machine particularly suited for performing in accordance with embodiments of the present system. The controller 104 may include one or more of a microprocessor, a processor, an application-specific or general-use integrated circuit(s), a logic device, etc. and/or combinations thereof. Further, the controller 104 may be a dedicated processor for performing in accordance with the present system or may be a general-purpose processor wherein only one of many functions operates for performing in accordance with the present system. The controller 104 may operate utilizing a program portion, multiple program segments, and/or may include a hardware device which may operate utilizing a dedicated or multi-purpose integrated circuit. In accordance with embodiments of the present system, the controller may include a plurality of processors or other logic devices which may be arranged in a distributed manner.

The pneumatic portion 110 may include one or more pumps, valves, mixers, actuators, gas conditioners (e.g., humidifiers, dehumidifiers, filters, etc.), pressure regulators, etc., which may operate under the control of the controller 104 so as to form a ventilation gas (VG) suitable for ventilating a patient. The VG may include one or more gasses, gas mixtures such as oxygen ($O_2$), nitrogen ($N_2$), air, etc. obtained from a gas supply interface 116 and/or from the atmosphere. The gas supply interface 116 may receive one or more gasses such as oxygen ($O_2$), nitrogen ($N_2$), air, etc. from a gas source such as such as a hospitals gas supply system, a reservoir, and/or compressed gas tanks.

The pneumatic interface 112 may couple the pneumatic portion 100 to a physical interface so that the VG may be provided to a user via the physical interface. The pneumatic interface 112 may include one or more pneumatic ports (e.g., 3 pneumatic ports) such as for example, patient and vent ports. The physical interface may include any suitable interface such as a non-invasive physical interface (e.g., a nasal cannula, a mask, etc.) or an invasive physical interface (e.g., an intubation tube, etc.) which may be coupled to the patient to provide the patient with the VG for inspiration and which may receive expiration gasses for further processing (e.g., for analysis, drying, remixing, etc.) In accordance with embodiments, the patient interface portion 112 may include inspiration and expiration legs (e.g., patient and vent legs, respectively which may couple to the patient and vent ports, respectively) to provide the ventilation gas for inspiration and receive the expiration gas for venting, respectively.

The sensors 108 may include or more sensors which may detect operating parameters of portions of the system 100 such as voltage, current, resistance, couplings, settings, parameters, etc. and form corresponding sensor information. For example, the sensors 108 may detect a coupling of the remote display 122 and/or display coupler 120 to the display interface 118 and may form corresponding information such as LUI presence information, LCD power good signals, etc. ventilation information (e.g., detected gas, percentage, PEEP, etc.). Further, the sensors may read an identification (ID) of one or more portions of the system 100 such as an ID of the remote display 122 and/or the display coupler 120 and form corresponding sensor information which may include information related to the ID. Further, the sensors 108 may detect characteristics of gasses within the system 100 such as the supply gasses, VG, expiration gasses (e.g., pressure, flow, density, composition, etc.) and may form corresponding sensor information. The sensor information may then be stored in a memory of the system for further analysis and/or rendered on a display of the system 100.

The UI 114 may include any suitable display device with which a user such as a clinician may interact with the system 100 under the control of the controller 104. The UI 114 may include any suitable touch-screen display with, for example, a display portion (e.g., an LCD screen), a touch-sensitive input device portion, and/or a backlight portion (as desired and/or available), etc., one or more of which may be enabled and/or disabled independently of each other. For example, the controller 104 may be operative to control one or more of these portions independently of each other. Further, the controller may include device drivers which may, for example, provide power to the remote display (e.g., to turn the remote display on or off, control the LCD screen of the remote display, control the backlight of the remote display, etc. The UI 114 may include at least one speaker, to render information. In accordance with embodiments of the present system, the UI 104 may render a graphical user interface (GUI) generated by the controller 102 and which may include information generated by the system such as ventilator information. The GUI may further include one or more selection and/or entry areas where a user may select and/or enter information such as system settings, selections, parameters, etc. Further, the GUI may be specific to a UI. For example, a GUI formed for rendering on the UI 114 (e.g., a BUIGUI as discussed herein) may differ from a GUI formed for rendering on the UI 122. The UI 114 may have a desired shape and/or size.

In accordance with embodiments of the present system, the UI 114 may include a touch-screen or other suitable input device such as a keyboard (hard of soft), a mouse, a pointer, a rotating dial, a slider, a touch-screen, etc. with which a user may enter information. The UI 114 may further include one or more illumination sources (e.g., lights, light emitting diodes, etc.) which may be operative under the control of the controller 104 such as a backlight.

The Remote UI 122 may include any suitable display device with which a user such as a clinician may interact with the system 100 under the control of the controller 104. The remote UI 122 may include any suitable touch-screen display with, for example, a display portion (e.g., an LCD screen), a touch-sensitive portion, and/or a backlight portion (if desired), etc., one or more of which may be enabled and/or disabled independently of each other. For example, the controller 104 may be operative to control one or more of these portions to turn on/off independently of each other. Further, the UI 114 may include a speaker. In accordance with embodiments of the present system, the remote UI 122 may render a graphical user interface (GUI) generated by the controller 102 such as a LUIGUI as discussed herein. The GUI may include one or more selection and/or entry areas where a user may select and/or enter information such as system settings, selections, parameters, etc. The remote UI 122 may have a desired shape and/or size which may differ from shape and/or size of the UI 104. For example, the remote UI 122 may have a similar shape as the UI 114, however, the UI 114 may be larger in size (e.g., in area) than equivalent dimensions of the UI 114. Accordingly, the remote UI 122 may have different display capabilities than the UI 122 such as enhanced display, history, settings, settings adjustment capability, animation, help support, and/or enhanced control such as gesture or haptic feedback, etc.

The remote UI 122 may be coupled to the display interface 118 via the display coupler 120 which may include an integrated power, video, and control lines. For example, the display coupler 120 may include integrated proximal and distal end couplers which may be identical to or different from each other. Each of the proximal and distal end couplers (generally end couplers) may integrate power, video, and control signals. Thus, only a single cable and corresponding end coupler may be required to be coupled to the display interface 118 to couple the remote display 122 to the ventilator 102. In accordance with embodiments, one or more of the end couplers may be of a quick disconnect type.

Figure 2:
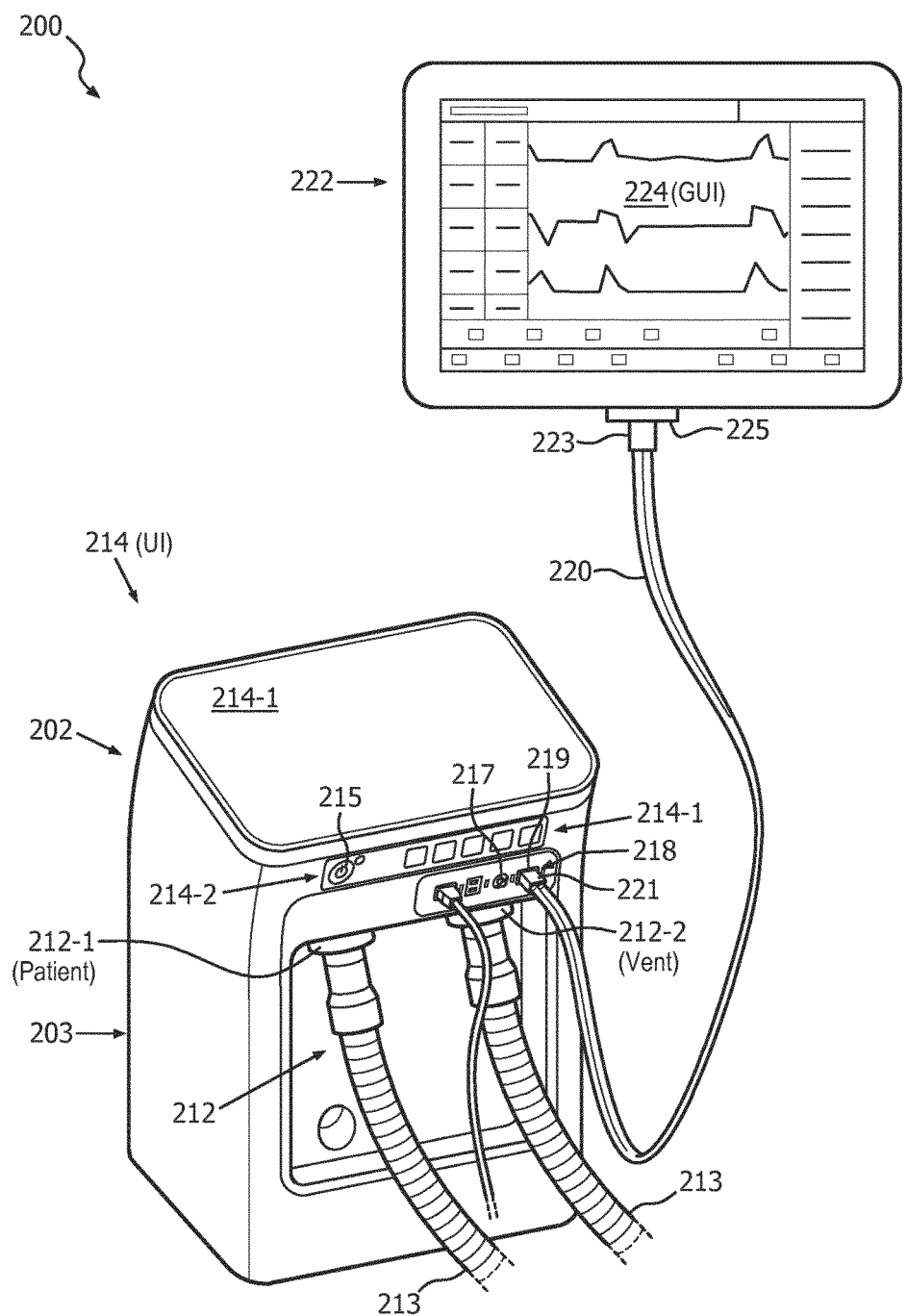
FIG. 2 shows a perspective front view of a portion of a ventilator system operating in accordance with embodiments of the present system.

FIG. 2 shows a perspective front view of a portion of a ventilator system 200 (hereinafter system 200) operating in accordance with embodiments of the present system. The system 200 may be similar to the system 100 and may include one or more of a ventilator 202, a user interface (UI) 214, a pneumatic interface 212, a display interface 218, a display coupler 220, and a remote user interface 222 (hereinafter remote display 222) which may be similar to the ventilator 102, the user interface (UI) 114, the pneumatic interface 112, the display interface 118, the display coupler 120, and the remote display 122, respectively. However, the user interface 214 may include a primary display 214-1 and hard key (HK) interface 214-2. The primary display 214-1 may include push-buttons, etc., and the HK user interface 214-2 may include push-buttons, knobs, etc., for selecting functions of the ventilator 202 and illumination sources (e.g., light-emitting diodes (LEDs), etc.) which may indicate whether a function is on or off. The HK user interface 214-2 may include a display select (Display Select) key 217 which, when depressed, may cause an active display to be toggled between the primary display 214-1 and the remote display 222, and an on/off key 215 selection of which may toggle the ventilator 202 on or off depending upon a current state.

In accordance with embodiments of the present system, when the display select key 217 is depressed, the controller may generate a display select request (e.g., signal) and when the on/off key 215 is depressed, the controller may generate a shutdown request (signal). These signals are discussed in more detail below. It is also envisioned that the display select key and the on/off key may be represented using soft keys such as soft keys which may be rendered on an active display of the system 200 using, for example, a corresponding menu item.

The controller may determine the ventilator information (VI) and form a graphical user interface (GUI) which may then be rendered on an active display such as the primary display 214-1 or the remote display 222. The controller may determine a display which is active and may generate a GUI, such as GUI 224, in accordance with display rules that may be tailored for the active display screen. For example, as is apparent, the remote display 222 may have additional display and/or input/output capabilities as compared to the primary display 214-1. Accordingly, the display rules may provide for additional display and/or settings rendering and/or input/output capabilities (e.g., settings adjustments) on the remote display 222 than is provided on the primary display 214-1. In accordance with embodiments of the present system, the primary display 214-1 may not be configurable in which case, there may need not be display rules with regard to this display. The controller may further render the UI or portions thereof as audio information using one or more speakers.

The ventilator 202 may further include a body 203 which may include one or more cavities in which portions such as a controller, a pneumatic portion, sensors, a memory, etc., may be located. The pneumatic interface 212 may include a plurality of pneumatic ports such as a patient port 212-1 which may receive VG for inspiration by the patient and a vent port 212-2 which may receive expiration gasses from the patient and/or excess VG. However, other ports are also envisioned. A patient interface 213 may include one or more pneumatic hoses 213 which may be coupled to corresponding pneumatic ports (e.g., 212-1, 212-2, etc.) of the pneumatic interface 212.

The display coupler may 220 include first and second ends 221 and 223, respectively, which may be the same as or different from each other. These ends (221 and 223) may be known as display coupler end plugs and may be of a quick-disconnect-type in accordance with embodiments. The first end 221 may be coupled to a receptacle 219 of the display interface 218 and the second end 223 may be coupled to a receptacle 225 of the remote display 222. In accordance with embodiments, the display interface 218 may be located on another side of the ventilator 202, such as on a side opposite to the pneumatic interface 212 (e.g., on a backside of the ventilator 202).

In accordance with embodiments of the present system, each of the first and second ends 221 and 223 may integrate power, video, audio, and/or control functions provided by the display. Thus, in accordance with embodiments, each of the end plugs may be a unitary plug which may couple the video, control, and power signals, carried between the ventilator 202 and the display coupler 220 that renders the remote display 222. In this way, a single cable may utilized between the ventilator 202 and the display coupler 220 as opposed to two or more cables to provide these functions.

For example, the display coupler 220 may carry standard serial video signals, control signals, and power to couple the remote display 222 to the ventilator 202 using the single cable. The control signals may be exchanged between the remote display 222 and the ventilator 202 using any suitable communication bus such as multi-master, multi-slave, single-ended, serial communication bus or the like. One such suitable communication bus that may be suitably utilized is an Inter-Integrated Circuit ($I^2C$) communication bus. Accordingly, the communication signals such as the control signals on this bus may follow a corresponding communication protocol such as the $I^2C$ protocol operating in accordance with embodiments of the present system.

The receptacle 219 may be configured to receive and couple to the first end 221 of the display coupler 220. The remote display 222 may include a receptacle 225 which may be configured to receive and couple to the second end 223 of the display coupler 220. In this way, the display coupler 220 may couple the remote display 222 to a controller of the ventilator 202.

The controller may generate a GUI 224 which may be rendered by the controller on the remote display 222, if desired. For example, upon detecting that the remote display 222 is coupled to the ventilator 202, the controller may generate and render (e.g., on the remote display 222) the GUI 224 which may include ancillary functionality compared to a GUI generated for rendering on the local display 214. In accordance with embodiments, the display 222 may also support, for example, a nurse call connection to enable the display 222 to support a nurse call function. In accordance with embodiments, the second end 223 may be configured to support one or more different monitors, such as an external projector or other large display. Further, remote display 222 may support an enhanced GUI interface as compared to the primary display 214-1 such as more info, help, expert settings, animation, etc.

In accordance with embodiments, the remote display 222 may be directly DC powered by the ventilator 202 through the display coupler 220. In accordance with embodiment, this power may be switch on for example only when a (working) remote display is connected. In accordance with embodiments, the connection cable (e.g., display coupler 220) may include a video coupling, such as one or more differential twisted pairs (e.g., 4) for the video signal, a control coupling, such as one or more (e.g., 2) twisted pair for I2c control and/or one or more power couplings, such as multiple lines for DC power and returns. In accordance with embodiments, the cable may be fully shielded for EMI control.

For example, in accordance with embodiments, the ventilator may provide DC power for the remote display when the ventilator is running on AC power. When running on battery the ventilator may be configured to switch to the BDU display and shut off the remote display to save power to extend running time for ventilation when AC power is interrupted.

Figure 3A:
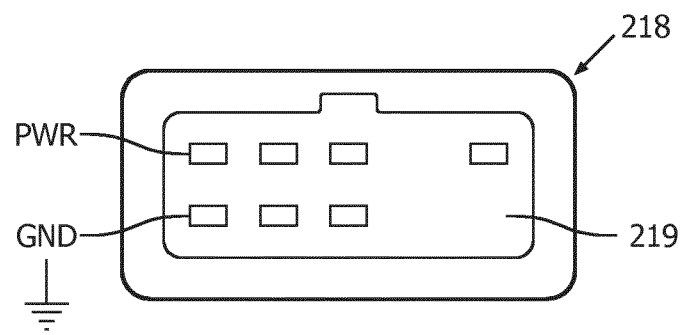
FIG. 3A shows a front planar view of the receptacle of the display interface in accordance with embodiments of the present system.

FIG. 3A shows a front planar view of the receptacle 219 of the display interface 218 in accordance with embodiments of the present system. For the sake of clarity, it will be assumed that the receptacle 225 of the remote display 222 may be similar to the receptacle 219 however, in accordance with further embodiments, the receptacle 225 and the receptacle 219 may be different connectors, such as different styles of connectors (e.g., connector for the ventilator may be an XLR-type connector while the connector to the remote display may be a video-type connector such as a D-sub-type connector.

Figure 3B:
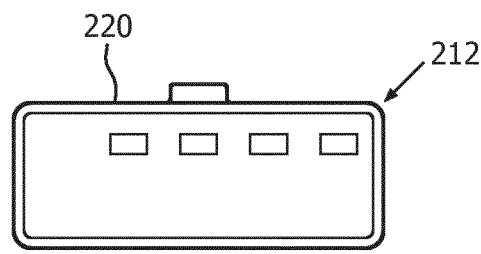
FIG. 3B shows a planar view of the first end of the display coupler in accordance with embodiments of the present system.

FIG. 3B shows a planar view of the first end 221 of the display coupler 220 in accordance with embodiments of the present system. The first end 121 may include an integrated coupler for power, control, and video signals and may be similar to the second end 223 of the display coupler 220. Quick-release-type latches may be provided to lock the first end 221 to the receptacle 219.

Figure 4:
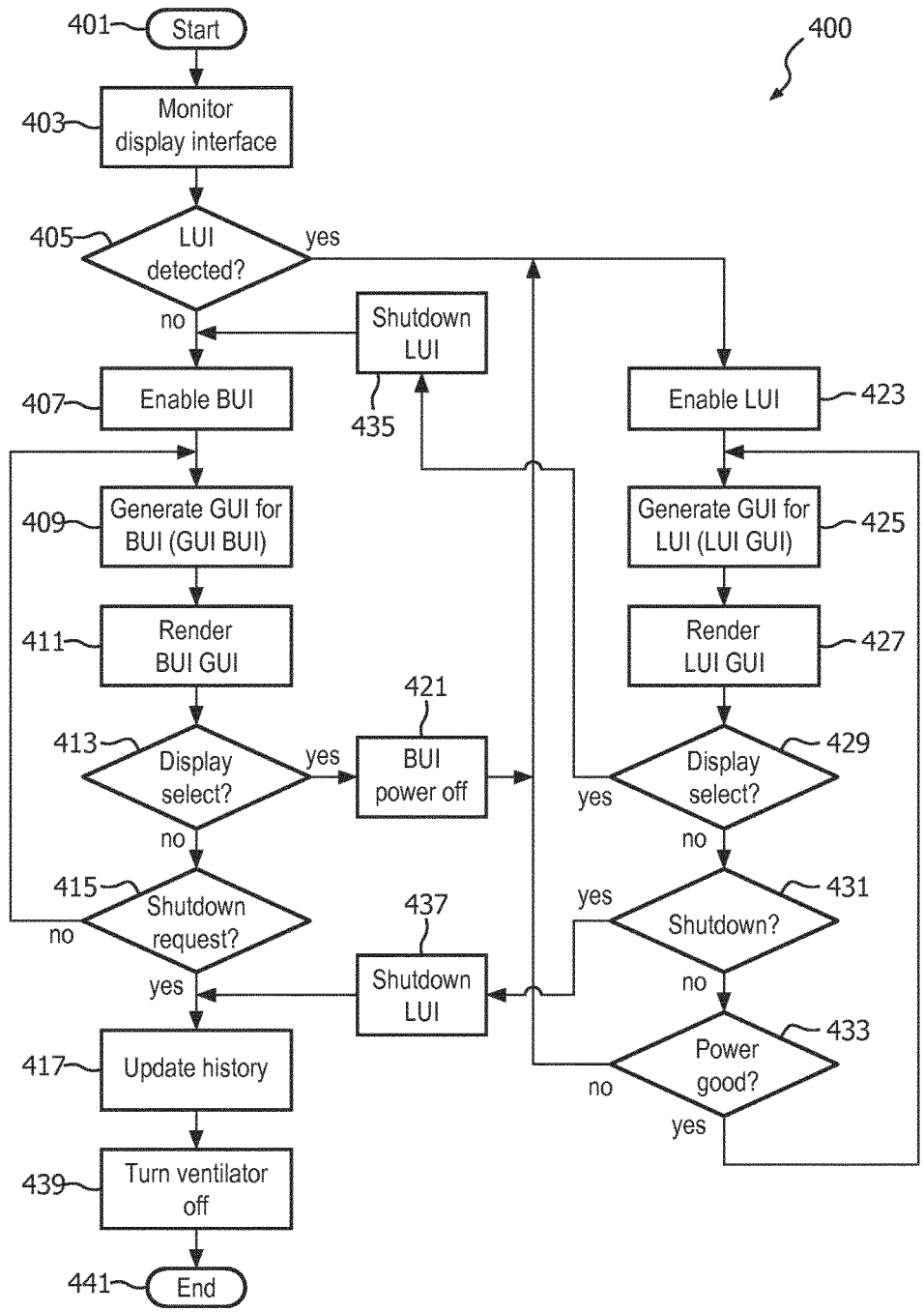
FIG. 4 shows a functional flow diagram that a process may perform in accordance with embodiments of the present system.

FIG. 4 shows a functional flow diagram that a process 400 (hereinafter process 400) may perform in accordance with embodiments of the present system. The process 400 may be performed using one or more computers communicating over a network and may obtain information from, and/or store information to one or more memories which may be local and/or remote from each other. The process 400 may include one of more of the following acts. The acts of process 400 may be performed using a ventilator systems operating in accordance with embodiments of the present system. Further, one or more of these acts may be combined and/or separated into sub-acts, as desired. Further, one or more of these acts may be skipped, for example, depending upon settings. In operation, the process may start during act 401 and then proceed to act 403. Control acts performed by the process 400 may be transmitted and/or received using any suitable communication system or protocol such as defined by the $I^2C$ protocol.

During act 403, the process may monitor a display interface ((DI), e.g., see, 118) to determine whether an LUI is detected. Accordingly, for example, the process may monitor control lines of the DI to determine whether any devices are coupled to the control lines. Accordingly, in a case wherein any devices are determined to be coupled to the DI, the process may communicate with the device to determine whether it is an LUI. For example, the process may request a device ID from the device which ID may be used to determine whether the device is an LUI (e.g., using a look-up table which may include device IDs and type of device (e.g., type=LUI). After completing act 403, the process may continue to act 405.

During act 405, the process may determine whether an LUI is detected. In this way, embodiments of the present system may select the LUI for providing display and/or input/output capabilities when it is detected and may otherwise select the BUI when an LUI is not detected. Thus, in accordance with embodiments, the process may be performed to select for example display information for rendering on the BUI and/or the LUI. During act 407, when an LUI is not detected, the process may enable the BUI for use with the system. Accordingly, the process may initialize the BUI so that it may be enabled to render information for the user to view and/or to receive user input. Accordingly, the process may, for example, perform actions to enable the BUI as described below with respect to FIG. 5 and the corresponding text. For example, acts to initialize the BUI are described with reference to acts 505-511 of FIG. 5. Once enabled, the BUI may be considered an active display. In accordance with embodiments of the present system, the BUI may be enabled even when a LUI is detected during act 405. Further, the BUI may have a default and/or set operation, display, etc., that is unaffected by whether a LUI is detected or not. However, in accordance with embodiments, the BUI interface may be adjusted depending on whether or not a LUI is detected. After completing act 407, the process may continue to act 409.

During act 409, the process may generate a graphical user interface (GUI) for display on the BUI. The process may form this GUI in accordance with settings and/or parameters of the BUI. Accordingly, this GUI may be referred to as a BUI GUI. However, in accordance with yet other embodiments, the GUI may be generic regardless of whether it is formed for the BUI connected or not to the LUI. After completing act 409, the process may continue to act 411.

During act 411, the process may render the generated GUI on the BUI. Accordingly, the process may transmit the GUI to the BUI for rendering. During this act the process may further monitor the touch-screen input as well as other user interfaces of the ventilator 202 for user inputs and may take appropriate actions based upon the user input(s). After completing act 411, the process may continue to act 413.

During act 413, the process may determine whether a display select was requested. Accordingly, if it is determined that the display select was requested, the process may continue to act 421. However, if it is determined that the display select was not requested, the process may continue to act 415. The display select may be determined to be requested based upon the display select information.

During act 415, the process may determine whether a shutdown is requested. Accordingly, in a case wherein it is determined that a shutdown is requested, the process may continue to act 417. However, in a case wherein it is determined that no shutdown is requested, the process may repeat act 409. A shutdown may be determined to be requested based upon shutdown information which may be generated when a user selects a shut-down key or in response to a system request for a shutdown.

During act 421, the process may shutdown the BUI. Accordingly, the process may disable drivers which may be driving the BUI and/or may turn off main power to the BUI and may thereafter continue to act 421. In accordance with some embodiments, the process may await a predefined period of time before shutting off the BUI (e.g., 2 seconds, etc.) so that the LUI may be powered up and/or enabled. In yet other embodiments, the process may await a signal from the LUI indicating that it is ready to be enabled before shutting off power to the BUI.

During act 423 following detection of the LUI, the process may enable the LUI for example for use as a touch-sensitive display of the system. Accordingly, the process may initialize the LUI (e.g., using an LUI initialization routine) so that it may be enabled to render information for the user to view and/or to receive a user input. Accordingly, the process may, for example, perform actions to enable the LUI as described below with respect to FIG. 5 and the corresponding text. For example, acts to initialize the LUI are illustratively described with reference to acts 513 through 527. Note acts of enabling the LUI may be different from that of the BUI. Accordingly, the process may follow an LUI initialization routine for example as defined by acts 513 through 527 which may be defined by the process and/or user and stored in a memory of the system. In accordance with embodiments, during act 423, the process may determine whether there is a power good indication (PGI). In these embodiments, in a case wherein it is determined that there is no power good indication (PGI), the process may shutdown the LUI (if on) and/or its drivers and repeat act 407. After completing act 423, the process may continue to act 425.

During act 425, the process may generate a GUI for the LUI. This act may be similar to act 409 where the process generates the GUI for the BUI. Accordingly, the process may refer to system settings for the LUI to determine an appropriate UI for the LUI. Once enabled, the LUI may be considered an active display and/or input/output device. After completing act 425, the process may continue to act 427. During act 427, the process may render the GUI generated during act 425 on the LUI. Accordingly, the process may transmit this GUI over display coupler to the LUI for rendering. During this act, the process may further monitor for example a touch-screen input of the LUI for user input(s) and may take appropriate actions based upon the determined user input(s). In accordance with embodiments, act 427 may be repeated as the LUI GUI is manipulated. After completing act 427, the process may continue to act 429.

During act 429, the process may determine whether a display select is requested. Accordingly, in a case wherein it is determined that the display select is requested, the process may continue to act 435. However, in a case wherein it is determined that the display select was not requested, the process may continue to act 431. During act 431, the process may determine whether a shutdown is requested. Accordingly, in a case wherein it is determined that a shutdown is requested, the process may continue to act 437. However, in a case wherein it is determined that no shutdown is requested, the process may continue to act 433. A shutdown may be determined to be requested based upon shutdown request information which may be generated when a user requests a shutdown selection (e.g., a hard or soft key, etc.) and/or when the system requests a shutdown as discussed with respect to act 415.

During act 433, the process may determine whether there is a power good indication (PGI). Accordingly, in a case wherein it is determined that there is a power good indication (PGI), the process may repeat act 425. However, in a case wherein it is determined that there is no power good indication (PGI), the process may repeat act 423. In accordance with embodiments of the present system, the power good indication (PGI) may be generated when power sensed at the power bus of the LUI is determined to be within a desired range of values and/or greater than a threshold value, as may be set by the system settings. For example, the process may determine whether voltage at a power bus (e.g., as measured at a display coupler input of the remote UI) is greater than a threshold voltage value (e.g., 5 volts, however other values and/or ranges of values may be suitably applied). Accordingly, in a case wherein it is determined that voltage at the power bus is greater than the threshold voltage value, the process may generate the power good indication (PGI). However, in a case wherein it is determined that the voltage at the power bus is not greater than (e.g., less than or equal) the threshold voltage value, the process does not generate the power good indication (PGI). Thus, the system may generate the power good indication (PGI) in real time based upon sensed main power characteristics at the LUI.

It is further envisioned that in accordance with embodiments of the present system, the power good indicator (PGI) may be generated only when mains power as opposed to internal battery power (e.g., emergency power) of the ventilator.

During acts 435 and 437, the process may shutdown the LUI. During this act, for example, the process may perform an LUI shutdown procedure for the LUI which may disable LUI video drivers and turn the LUI LCD power off. In accordance with embodiments, the LUI shutdown procedure may for example be set/reset by the system and/or user and may be stored in a memory of the system. For example, in embodiments the LUI shutdown procedure may include one or more desired acts such as shutdown LUI LCD power, update BUI display/control operations (in a case wherein the BUI GUI is changeable or otherwise programmable), etc. After completing act 435, the process may continue to act 407; and after completing act 437 the process may continue to act 417.

During act 417, the process may update history information and store the updated history information in a memory of the system for later use. The history information may include ventilator parameters, settings, user information (e.g., user settings, user preferences, user ID, user password, etc.), patient information (e.g., patient ID, preferred parameters, etc.) and/or information generated by the process, etc. The updated history information may then be accessed at a later time for viewing and/or further analysis. After completing act 417, the process may continue to act 439.

During act 439, the process may perform a ventilator shutdown procedure to shut down the ventilator. The ventilator shutdown procedure may simply turn off main power to the ventilator or may include one or more predefined acts (as may be defined in a shutdown process of the system and stored in a memory of the system) such as turning off the LUI, purging lines (e.g., to clear condensation, dirt, etc. from these lines), closing valves (e.g., to stop gas flow therefrom), etc. After completing act 439, the process may continue to act 441 where the process may end.

Figure 5:
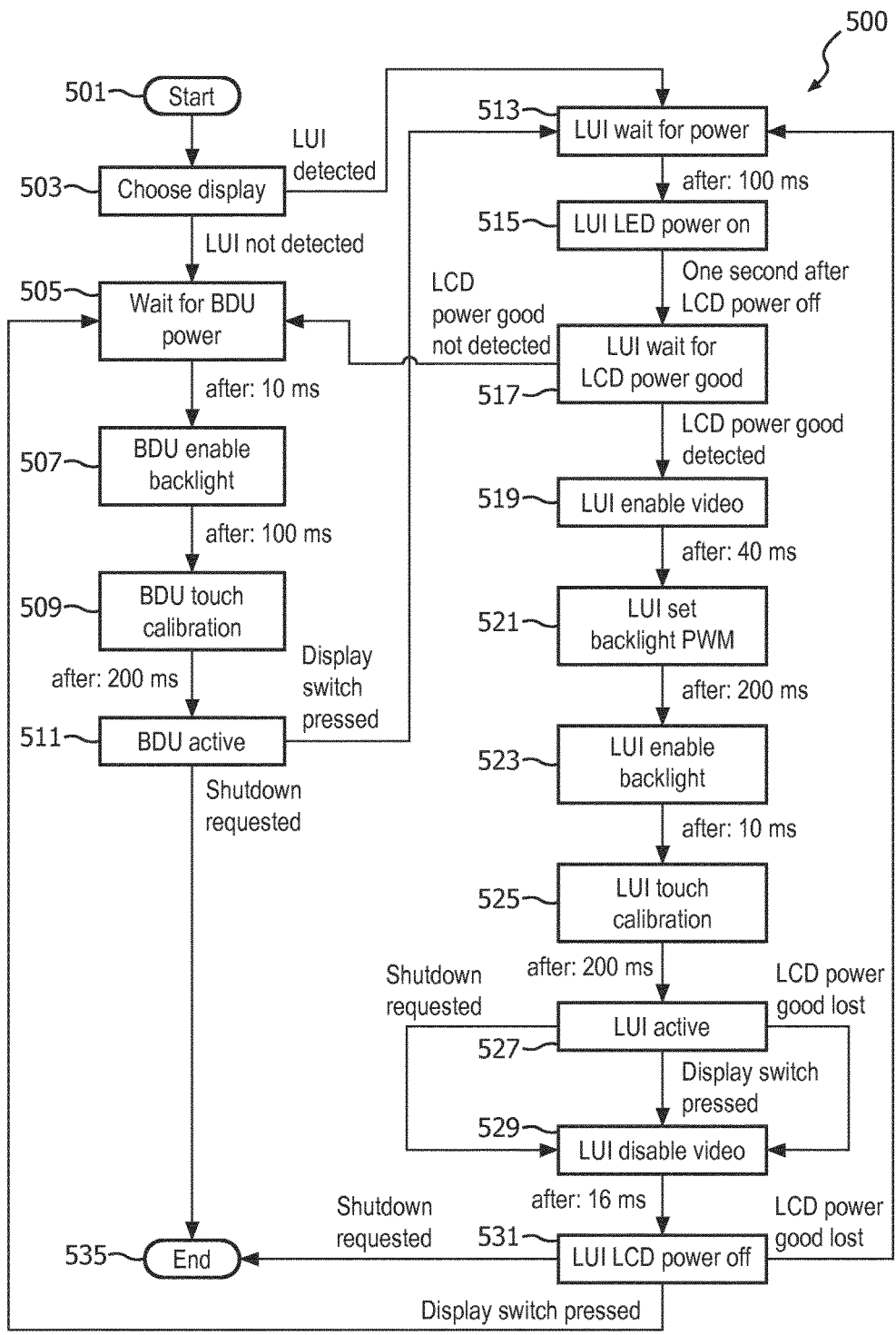
FIG. 5 shows a functional flow diagram that a process may perform in accordance with embodiments of the present system.

Table 1 illustrates a process including a plurality of acts one or more of which may be performed in accordance with embodiments of the present system and will be described in further detail with reference to FIG. 5. FIG. 5 shows a functional flow diagram that process 500 may perform in accordance with embodiments of the present system. With reference to Table 1, each act may be represented as a state and may include corresponding entry action(s), transition event(s), exit action(s), and a next state. In accordance with embodiments of the present system, the entry action may be associated with each act and may be performed during the act. In accordance with embodiments, the transition event(s) associated with each act may, if met (e.g., as may be determined by the process), define one or more acts to perform when the corresponding transition event is determined to occur. Lastly, the exit action(s) associated with each event may define actions which occur when exiting the corresponding act. With regard to the acts, entry and exit actions of a corresponding act will be described with reference to a corresponding act or a next act for brevity. Moreover, certain actions may occur after exemplary time periods for each corresponding state to have elapsed (e.g., with respect to act 503, actions may occur after 110 ms elapses). However, other time periods may be suitably utilized. Further, for the sake of clarity, these time periods are illustrated in Table 1 and may not be discussed with regard to the detailed description of FIG. 5.

Referring FIG. 5, the process 500 may be performed using one or more computers communicating over a network and may obtain information from, and/or store information to one or more memories which may be local and/or remote from each other and like the process 400, the process 500 may include one of more of the following acts. In operation, the process may start during act 501 and then proceed to act 503. Control acts performed by the process 500 may be transmitted and/or received using any suitable communication system or protocol such as a multi-master multi-slave serial computer bus protocol such as defined by the I²C protocol. The acts of process 500 may be defined by the system and/or user and/or may be stored in a memory of the system for later use. Further, during the process 500 when enabling drivers for example, the process may initialize the drivers (e.g., using setting information obtained from a memory of the system) and/or may otherwise enable the corresponding drivers so that these drivers may generate corresponding signals (e.g., video drives may generate video signals, and or other processes, drivers, etc.).

TABLE 1

| State (no.) | Entry Action | Transition Event | Exit Action | Next State |
|---|---|---|---|---|
| Choose Display (503) | None | LUI not detected after 110 msec. (e.g., LUI not present) | Enable BDU LCD power | BDU Wait for Power |
| | | LUI Detected with 110 msec. (e.g., LUI present) | Enable LUI main power | LUI Wait For Power |
| BDU Wait For Power (505) | None | 10 msec. elapses | Enable BDU LCD video | BDU Enable Backlight |
| BDU Enable Backlight (507) | None | 100 msec. elapses | Set BDU backlight PWM | BDU Touch Calibration |
| BDU Touch Calibration (509) | None | 200 msec. elapses | Enable touch controller | BDU Active |
| BDU Active (511) | Initialize touch controller | Display switch pressed and LUI is present (e.g., detected during act 503) | Enable LUI main power | LUI Wait For Power |
| | | Shutdown Requested | Disable BDU | Shutdown |
| LUI Wait for Power (513) | None | 100 msec. elapses | Initialize LUI I/O expander | LUI LCD Power On |
| | | LUI Disconnected | Disable LUI Enable BDU LCD power | BDU Wait For Power |
| LUI LCD Power On (515) | None | 1000 msec. since LUI LCD power off elapses | Enable LUI LCD power | LUI Wait for Power Good |
| | | LUI Disconnected | Disable LUI Enable BDU LCD power | BDU Wait For Power |
| LUI Wait for Power Good (517) | None | LUI LCD Power Good detected (e.g., PGI detected) | None | LUI Enable Video |
| | | LUI LCD Power Good not detected (e.g., no PGI) | Shut off LUI main and LCD power, post alert Enable BDU LCD power | BDU Wait For Power |
| | | LUI Disconnected | Disable LUI Enable BDU LCD power | BDU Wait For Power |
| LUI Enable Video (519) | None | 40 msec. elapses | Enable LUI LCD video Disable BDU | LUI Set Backlight PWM |
| | | LUI Disconnected | Disable LUI Enable BDU LCD power | BDU Wait For Power |
| LUI Set Backlight PWM (521) | None | 200 msec. elapses | Set LUI backlight PWM | LUI Enable Backlight |
| | | LUI Disconnected | Disable LUI Enable BDU LCD | BDU Wait For Power |

TABLE 1-continued

| State (no.) | Entry Action | Transition Event | Exit Action | Next State |
|---|---|---|---|---|
| LUI Enable Backlight (523) | None | 10 msec. elapses | Enable LUI backlight | LUI Touch Calibration |
| | | LUI Disconnected | Disable LUI Enable BDU LCD power | BDU Wait For Power |
| LUI Touch Calibration (525) | None | 200 msec. elapses | Enable touch controller Load LUI EEPROM data | LUI Active |
| | | LUI Disconnected | Disable LUI Enable BDU LCD power | BDU Wait For Power |
| LUI Active (517) | Initialize touch controller | Display switch pressed LUI LCD Power Good Lost Shutdown Requested | Disable LUI backlight and touch controller | LUI Disable Video |
| | | LUI Disconnected | Disable LUI Enable BDU LCD power | BDU Wait For Power |
| LUI Disable Video (529) | None | 200 msec. elapses | Disable LUI video | LCD LUI Power Off |
| | | LUI Disconnected | Disable LUI Enable BDU LCD power | BDU Wait for Power |
| LUI LCD Power (531) | None | 16 msec. elapses and display switch was pressed LUI active state | Turn off LUI LCD power Enable BDU LCD power | Wait for BDU Power |
| | | 16 msec. elapses and LUI LCD Power Good was lost in LUI active state | Enable LUI main power | Wait for LUI Power |
| | | 16 msec. elapses and shutdown requested in LUI active state | None | Shutdown |
| | | LUI Disconnected | Disable LUI Enable BDU LCD power | BDU Wait For Power |
| Shutdown (Final State) (535) (END) | Turn off LUI main power | Never leaves this state | Never leaves this state | Never leaves this state |

During act 503, the process may choose (e.g., select) a display. Accordingly, the process may determine whether the LUI is detected and when the LUI is detected, the process may enable LUI main power and continue to act 513. However, in a case wherein the LUI is not detected the process may enable BDU LCD power and continue to act 505. In accordance with embodiments of the present system, the process may determine that an LUI is detected using any suitable method such as by monitoring control lines of a display interface (e.g., see 118, FIG. 1) to determine whether any device(s) are connected thereto, by checking an ID of the device, etc. In accordance with embodiments of the present system, the process may compare the ID of the device with those stored in a memory of the system to determine whether the device is an LUI and/or other functionality of a connected device. Accordingly, in a case wherein the device is determined to be an LUI, the process may determine that the LUI is detected.

In a case wherein the LUI is not detected, the process may enable BDU LCD power using any suitable method such as by signaling a power switch of the BDU to turn on (e.g., this may be considered a main BDU power) and/or to supply power to the LCD of the BDU. The method used to turn on the LCD of the BDU may be dependent upon design of a power bus of the BDU. For example, in accordance with some embodiments, the process may enable LCD drivers to drive the BDU LCD.

In a case wherein the LUI is detected, the process may enable LUI main power (e.g., turn on the LUI) using any suitable method such as by signaling (e.g., over the control lines) a power switch of the LUI to turn on (e.g., this may be considered a main LUI power) the LUI. The method used to turn on the LUI may be dependent upon design of a power bus of the LUI and/or other capabilities of a given LUI.

During acts 505 through 509, the process may initialize the BDU. In accordance with embodiments of the present system, these acts may be considered BDU initialization acts. Similarly, during acts 513 through 525, the process may initialize the LUI and these acts may be considered initialization acts similarly.

During act 505, the process may wait for the BDU power to be provided. Further, the process may enable BDU LCD video drivers to drive the BDU LCD and may enable BDU backlight drivers as discussed herein. Accordingly, the BDU LCD video drivers may be configured to drive the LCD of the BDU. After completing act 505, the process may continue to act 507.

During act 507, the process may set the BDU backlight drivers to provide a desired amount of power to the BDU backlight so that the BDU backlight may provide a desired amount of illumination. The process may do this using any suitable method such as by controlling power signals (e.g., pulse-width modulated PWM signals) generated by the BDU backlight drivers and which may drive the BDU backlight so that a desired amount of illumination is provided by the backlight of the BDU.

During act 509, the process may perform a BDU touch calibration and may thereafter enable the BDU touch (screen) controller. Accordingly, the process may control BDU touch-screen drivers to perform the BDU touch calibration and thereafter enable the touch-screen drivers so that the touch-screen (e.g., of the BUI) may be enabled so that it may be used as an input device to receive one or more touch selection(s). After completing act 509, the process may continue to act 511.

During act 511, the BDU may be active to render information generated by the ventilator system or portions thereof such as ventilator information. Accordingly, during this act the BDU may render information provided thereto such as a GUI generated by the controller. During this act, the BDU touch controller may determine input(s) thereto and form corresponding touch information which may be provided to the controller for further processing.

Further, during this act the process may determine whether an LUI is connected and/or whether a connected LUI is powered on, such as through actuation of a display select. Accordingly, in a case wherein a connected LUI is powered on, the process may enable LUI main power (e.g., turn main power to the LUI on) and continue to act 513.

During act 511, the process may determine whether a shutdown request has been generated. Accordingly, in a case wherein a shutdown request has been generated, the process may disable the BDU (e.g., by disabling (device) drivers of the BDU) and thereafter continue to act 535 where the process may end. By disabling the BDU, the process may turn off (e.g., disable) the backlight, the touch controller, and/or the LCD video signals, for the BDU using any suitable method such as by disabling the corresponding device drivers for the BDU such as the BDU backlight driver, the BDU touch controller driver, and the LCD video signal driver, respectively.

During one or more of acts 513 through 531, the process may determine whether the LUI is disconnected. The process may do this by determining whether the LUI is detected similarly to the method discussed above with respect to act 503. Accordingly, in a case wherein it is determined that the LUI is detected, the process may continue to perform a corresponding act of the acts 513 through 531. However, in a case wherein it is determined that the LUI is not detected, the process may disable the LUI similarly to the method used to disable the BUI as discussed above with respect to act 511. However, when disabling the LUI, the process may further disable LUI main power (e.g. turn main power to the LUI off). With respect to disabling the LUI, the process may turn off (e.g., disable) one or more of the LUI backlight, the touch controller, and the LCD video signals, for the LUI using any suitable method such as by disabling the corresponding device drivers such as the LUI backlight driver, the LUI touch controller driver, and the LUI LCD video signal driver, respectively. In a case wherein the LUI is disabled, the process may enable BDU power (e.g., see acts 503, 505, etc.) and thereafter continue to act 505. These determinations may have priority over other determinations within the corresponding acts. When the LUI is determined to be present, the device drivers for the LUI may be configured for driving the LUI during an LUI initialization as described with reference to acts 513 through 525.

During act 513, the process may wait for LUI power for a threshold wait time to elapse (e.g., 100 ms). This threshold wait time may allow LUI power to enabled, stabilized, etc. For example, the process may wait for the LUI main power for a threshold wait time to elapse. After completing act 513, the process may continue to act 515.

During act 515, the process may enable the LUI LCD power. The process may enable LUI LCD power using any suitable method such as by signaling a power switch of the LUI to turn on and/or to supply power to the LCD of the LUI. The method used to turn on the LCD of the LUI may be dependent upon design of a power bus of the LUI and/or other considerations/capabilities of the LUI. For example, in accordance with some embodiments, the process may enable LCD drivers to drive the LUI LCD. Thereafter, the process may continue to act 517.

During act 517, the process may enter an LUI Wait for Power Good state where the process may determine whether a power good indication (PGI) has been generated. Accordingly, in a case wherein it is determined that a power good indication (PGI) has been generated, the process may continue to act 519. However, in a case wherein it is determined that a power good indication (PGI) has not been generated, the process may perform an LUI shutdown for example by shutting off the LUI LCD power and then the LUI main power, posting an alert (e.g., using a rendering device of the system) to inform a user of the lack of a good power indication (e.g., poor power available) at the LUI, enabling the BDU LCD power (e.g., as discussed with respect to act 403), and thereafter continuing to act 505. As discussed elsewhere, the power good indication (PGI) may for example be generated in real time based upon sensed main power characteristics at the LUI. Further, the lack of a power good indication (PGI) may indicate that LCD power good is for example lost.

During act 519, the process may enable LUI LCD video drivers (e.g., enable LUI LCD video) to drive the LUI LCD, may though need not in some embodiments disable the BDU (e.g., see disabling BDU act 511), and may continue to act 521. The process may enable LUI LCD by enabling LUI LCD drivers to drive the LUI LCD in accordance with embodiments of the present system.

During act 521, the process may for example set backlight pulse-width modulation (PWM) drivers of the LUI so that a desired amount of power may be provided to the backlight of the LUI when enabled and may continue to act 523. Accordingly, the process may obtain desired display power settings for the corresponding display (e.g., LUI) from a memory of the system and may transmit these values to the LUI backlight PWM drivers so that they may provide a desired amount of power to the backlight of LUI display. As may be readily appreciated, in accordance with embodiments of the present system, the backlighting when present may be otherwise set.

During act 523, the process may enable the LUI backlight. Accordingly, the process may enable the backlight drivers and may thereafter continue to act 525. When enabled, the backlight drivers may drive the LUI backlight. During act 525, the process may perform an LUI touch calibration and/or may otherwise enable the LUI touch (display) controller. Accordingly, the process may control LUI touch screen drivers to perform the calibration and thereafter enable the touch screen of the LU) so that it may receive touch-screen input(s) and provide indication of such (e.g., touch-screen information) to the controller for further processing. After completing act 525, the process may continue to act 527.

During act 527, the LUI may be active to render information generated by the ventilator system or portions thereof and/or to receive input for further processing by the controller. Accordingly, during this act the LUI may render information provided thereto such as information generated by the system. Such information may include a GUI generated by the system such as the LUI GUI.

During this act, the process may further determine whether a display select was requested; whether a shutdown request was generated; and/or whether the LCD power good is lost while the LUI was active. In the affirmative to any of these conditions, the process may continue to act 529 where the process may disable (e.g., turn off) LUI LCD video drivers and thereafter continue to act 531. For example, the LCD power good may be lost when the LUI was previously active.

During act 531, the process may disable (e.g. turn off) LUI LCD power, and for example thereafter continue to act 505 as shown. For example, in a case wherein the process determines that the display select was requested, the process may turn off LUI LCD power, enable BDU LCD power, and thereafter continue to act 505. In another case, wherein the process determines that the LCD power good was lost while the LUI was active, the process may enable the LUI main power and may thereafter continue to act 513. In a case wherein it is determined that a shutdown request was generated, the process may continue to act 535.

Accordingly, embodiments of the present system may provide a ventilator which may detect whether a remote display is present (e.g., coupled thereto). Accordingly, when the remote display (e.g., secondary display) is determined to be present, a remote display initialization sequence may be performed. However, in a case wherein the remote display is determined not to be present, a local (e.g. local to the ventilation device) display initialization sequence may be performed. Further, a ventilator may detect a user's selection of the display selector switch and may switch in accordance with embodiments of the present system. The ventilator may detect whether the remote display is currently active when the selection switch is selected, and may turn off the remote display before or during switching the primary display on, for example when the remote display is currently active when the selection switch was selected. Further, the ventilator may detect a power good signal, and in a case wherein the power good signal is lost (e.g., not asserted or not found) for example during initialization of the remote display, the ventilator may begin an initialization of the local display. However, in a case wherein the power good signal is lost while the remote display is active, the ventilator may restart the initialization of the remote display.

In accordance with embodiments of the present system, the ventilator may include one or more printed circuit board assemblies (PCBAs) with specific interfaces and connectors which correspond with corresponding plugs of the display coupler. Similarly, the remote display may include corresponding interfaces and couplers to receive the display coupler and communicate with a controller of the ventilator. Accordingly, the display coupler may include a unitary housing within which one or more signals, such as serial video signals (e.g., standard serial video signals, etc.) are provided, control signals (e.g., I²C control signals) are provided and power (e.g., direct current (DC) or alternating current (AC) as may be desired) is provided between a ventilator and a remote touch-screen display coupled thereto. In accordance with embodiments, the display coupler may have a length of between about 1½ through 30 feet (e.g., about 0.5 to 10 meters) and may provide an integrated solution for ventilators such as mobile ventilators which may employ for example, secondary touch-screen displays with control and ancillary functionality such as input/output (I/O) functionality in accordance with embodiments of the present system.

Accordingly, embodiments of the present system may provide a ventilator with a remote display/input device that may be coupled together using a single integrated cable rather than having to couple separate power, serial video, and control signal cables. The ventilator may include a power supply which may provide main power to the remote display and which may be controlled by a controller of the ventilator. Further, although touch-screen type remote displays are discussed in the present application, it will be appreciated embodiments of the present system may be compatible with non touch-screen-type remote displays. Accordingly, the ventilator may employ other input devices (e.g., a keyboard, a mouse, a pointer, a stylus, a touch-pad, etc.) with which a user may interact when the remote display is not a touch-screen type display. Further, in accordance with embodiments, the present system may provide information on one or more of the BDU and LUI based on, for example, the input/output capabilities of a given LUI verses another given LUI. For example, in a case where a given LUI has touch-input capabilities, the present system may disable an input capability of the BDU when an LUI with input capabilities is detected, etc.

The methods of the present system are particularly suited to be carried out by processor programmed by a computer software program, such program containing modules corresponding to one or more of the individual steps or acts described and/or envisioned by the present system as discussed. Accordingly, embodiments of the present system may provide user interfaces (UIs) with displays and touch-screens of varying size. For example, a primary display may provide a first area and be situated on a mobile ventilator while a secondary display may have a second area and may be situated remotely from the ventilator. The ventilator may communicate with the secondary display using any suitable method or method such as using the I²C standard. The first area may be sized differently from the second area and may provide different input and output (e.g., rendering) capabilities.

While the present invention has been shown and described with reference to particular exemplary embodiments, it will be understood by those skilled in the art that present invention is not limited thereto, but that various changes in form and details, including the combination of various features and embodiments, may be made therein without departing from the spirit and scope of the invention. Further variations of the present system would readily occur to a person of ordinary skill in the art and are encompassed by the following claims.

Finally, the above-discussion is intended to be merely illustrative of the present system and should not be construed as limiting the appended claims to any particular embodiment or group of embodiments. Thus, while the present system has been described with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function;

e) any of the disclosed elements may be comprised of hardware portions (e.g., including discrete and integrated electronic circuitry), software portions (e.g., computer programming), and any combination thereof;

f) hardware portions may be comprised of one or both of analog and digital portions;

g) any of the disclosed devices or portions thereof may be combined together or separated into further portions unless specifically stated otherwise;

h) no specific sequence of acts or steps is intended to be required unless specifically indicated;

i) the term "plurality of" an element includes two or more of the claimed element, and does not imply any particular range of number of elements; that is, a plurality of elements may be as few as two elements, and may include an immeasurable number of elements; and j) the term and/or and formatives thereof should be understood to mean that only one or more of the listed elements may need to be suitably present in the system in accordance with the claims recitation and in accordance with one or more embodiments of the present system.

The invention claimed is:

1. A medical ventilator, comprising:
a first user interface having a touch-sensitive primary display having a first display area;
a hard key (HK) interface including a display select key;
a unitary display coupler configured to couple a remote user interface to the medical ventilator; and
at least one controller which is configured to:

determine whether the remote user interface having a touch-sensitive remote display is coupled to the medical ventilator, respond to the display select key of the HK interface to toggle an active display between the touch-sensitive primary display and the touch-sensitive remote display, wherein the medical ventilator is configured to directly provide DC power through the unitary display coupler to the touch-sensitive remote display while the medical ventilator is running on AC power, enable the first user interface when it is determined that the remote user interface is not coupled to the medical ventilator and enable the remote user interface when it is determined that the remote user interface is coupled to the medical ventilator, and sense when the medical ventilator switches from an external power source to an internal power source and in response, disable the remote user interface after the remote user interface is enabled and enable the first user interface after the first user interface is disabled.

2. The medical ventilator of claim 1, further comprising: a display interface configured to receive an end of the unitary display coupler.

3. The medical ventilator of claim 1, wherein the unitary display coupler is further configured to couple video and control signals to the remote user interface.

4. The medical ventilator of claim 1, wherein the at least one controller is further configured to generate a power good indicator based upon characteristics of power supplied by the ventilator to the remote user interface.

5. The medical ventilator of claim 4, wherein when the remote user interface is enabled, the at least one controller is further configured to determine whether the power good indicator is generated, and shut down the remote user interface when it is determined that the power good indicator is not generated.

6. The medical ventilator of claim 2, wherein when the remote user interface is enabled, the at least one controller is further configured to determine whether the remote user interface is decoupled from the ventilator.

7. The medical ventilator of claim 6, wherein when the at least one controller determines that the remote user interface is decoupled from the ventilator, the at least one controller is further configured to enable the first user interface.

8. The medical ventilator of claim 1, wherein the touch-sensitive remote display of the remote user interface has a second display area which is larger than the first display area of the touch-sensitive primary display of the first user interface.

9. The medical ventilator of claim 1, wherein the at least one controller is further configured to generate a first graphical user interface (GUI) when the first user interface is enabled and a second GUI, different from the first GUI, when the remote user interface is enabled.

10. The medical ventilator of claim 9, wherein the first GUI further comprises menu items which are defined for the first user interface and the second GUI further comprises menu items which are defined for the remote user interface.

* * * * *